(12) United States Patent
Roelvink et al.

(10) Patent No.: US 6,740,525 B2
(45) Date of Patent: May 25, 2004

(54) ADENOVIRAL CAPSID CONTAINING CHIMERIC PROTEIN IX

(75) Inventors: Petrus W. Roelvink, Olney, MD (US); Imre Kovesdi, Rockville, MD (US); Thomas J. Wickham, Germantown, MD (US)

(73) Assignee: GenVec, Inc., Gaithersburg, MD (US)

( * ) Notice: Subject to any disclaimer, the term of this patent is extended or adjusted under 35 U.S.C. 154(b) by 178 days.

(21) Appl. No.: 09/780,224

(22) Filed: Feb. 9, 2001

(65) Prior Publication Data

US 2001/0047081 A1 Nov. 29, 2001

Related U.S. Application Data

(60) Provisional application No. 60/181,163, filed on Feb. 9, 2000.

(51) Int. Cl.[7] .................. C12N 15/34; C12N 15/63; C12N 15/861; C07H 21/04; C07K 14/075
(52) U.S. Cl. ............. 435/456; 435/320.1; 435/235.1; 435/5; 435/6; 435/7.1; 435/455; 435/457; 435/325; 435/366; 435/236; 530/350; 530/324; 530/325; 530/326; 536/23.1; 536/23.4; 536/23.72
(58) Field of Search ................. 435/320.1, 235.1, 435/5, 6, 7.1, 455, 456, 457, 325, 366, 236; 530/350, 324, 325, 326; 536/23.1, 23.4, 23.72

(56) References Cited

U.S. PATENT DOCUMENTS 6,555,368 B1 * 4/2003 Curiel .................. 435/320.1

FOREIGN PATENT DOCUMENTS

| WO | WO 98/13485 A | 4/1998 |
|----|---------------|--------|
| WO | WO 98/40508 A | 9/1998 |
| WO | WO 99/36545 A | 7/1999 |
| WO | WO 01/21216 A | 3/2001 |

OTHER PUBLICATIONS

O'Riordan et al., *Hum. Gene Ther.*, 10 (8), 1349–1358 (May 20, 1999).
Akalu et al., *J. Virol.*, 73 (7), 6182–6187 (Jul. 1999).
Colby et al., *J. Virol.*, 39 (3), 977–980 (Sep. 1981).
Ghosh–Choudhury et al., *Embo J.*, 6 (6), 1733–1739 (1987).
Furcinitti et al., *Embo J.*, 8 (12), 3563–3570 (1989).
Lutz et al., *J. Virol.*, 71 (7), 5102–5109 (Jul. 1997).
Manuel et al., *Am. J. Physiol.*, 273, L741–L748 (1997).
Stewart et al., *Embo J.*, 12 (7), 2589–2599 (1993).

* cited by examiner

*Primary Examiner*—David Guzo
(74) *Attorney, Agent, or Firm*—Leydig, Voit & Mayer, Ltd.

(57) ABSTRACT

The present invention provides a chimeric protein IX (pIX). The chimeric pIX protein has an adenoviral pIX domain and also a non-native amino acid. Where the non-native amino acid is a ligand that binds to a substrate present on the surface cells, the chimeric pIX can be used to target vectors containing such proteins to desired cell types. Thus, the invention provides vector systems including such chimeric pIX proteins as well as methods of infecting cells using such vector systems.

46 Claims, 2 Drawing Sheets

Fig. 1B

|  |  | + Consensus #1 |
|---|---|---|
| ...DF...LA.S....R...ED.L..LLA.L..L.. | Consensus #1 |  |
| MAADFGFYNLLASSAGG----RSSAREDALTVLLATLESLT | Majority |  |
| 81 MAADFSFYNHLASNAVT----RTAVREDILTVMLAKLETLT | pIX-Ad12 | SEQ ID NO: 1 |
| 66 PEDQTPYMILVEDSLGGGLKRRRMDLLEESNQQLLATLNRLR | pIX-Ad3 | SEQ ID NO: 2 |
| 66 PEDQTPYMILVEDSLGGGLKRRRMDLLEESNQQLLATLNRLR | pIX-Ad7 | SEQ ID NO: 3 |
| 75 IVTDFAFLSPLASSAAS----RSSARDDKLTALLAQLDSLT | pIX-Ad2 | SEQ ID NO: 4 |
| 75 IVTDFAFLSPLASSAAS----RSSARDDKLTALLAQLDSLT | pIX-Ad5 | SEQ ID NO: 5 |
| 80 MAADFGLYNQLAAASR-L---RE-----EDALSVVLTRLEELS | pIX-Ad40 | SEQ ID NO: 6 |
| 80 MAADFGLYNQLAAASRSL---RE-----EDALSVVLTRMEELS | pIX-Ad41 | SEQ ID NO: 7 |

|  |  | + Consensus #1 |
|---|---|---|
| .L...SQ------L...P.N.V | Consensus #1 | SEQ ID NO: 8 |
| TQLAAVSQ------AALVGGSPPNAV | Majority | SEQ ID NO: 9 |
| 118 AQLEELSQKVEELAD------ATTHTPAQPVTQ | pIX-Ad12 |  |
| 106 TGLAAYVQ------ANLVGGQVNPFV | pIX-Ad3 |  |
| 106 TGLAAYVQ------ANLVGGQVNPFV | pIX-Ad7 |  |
| 112 RELNVVSQ------QLLDLRQQVSALKASSPPNAV | pIX-Ad2 |  |
| 112 RELNVVSQ------QLLDLRQQVSALKASSPPNAV | pIX-Ad5 |  |
| 113 QQLQDMSA------KMALLNPPANTS | pIX-Ad40 |  |
| 114 QQLQDLFA------KVALLNPPANAS | pIX-Ad41 |  |

Consensus 'Consensus #1': When 57% (4) match the residue of the Consensus show the residue of the Consensus, otherwise show '.'.

ADENOVIRAL CAPSID CONTAINING CHIMERIC PROTEIN IX

CROSS-REFERENCE TO RELATED PATENT APPLICATIONS

This patent application claims the benefit of U.S. Provisional Patent Application No. 60/181,163, filed Feb. 9, 2000.

FIELD OF THE INVENTION

This invention pertains to adenoviral capsids containing chimeric protein IX.

BACKGROUND OF THE INVENTION

Based on the popularity of adenoviruses as gene transfer vectors, efforts have been made to increase the ability of adenoviruses to enter certain cells, e.g., those few cells it does not infect and those cells they do not enter as well as would be desirable, sometimes selectively, an approach generally referred to as "targeting." Such efforts largely have centered on biochemical alteration of the proteins of the adenoviral coat, which include the fiber, penton, and hexon, as well as proteins IIIa, VI, and IX. Of these proteins, the trimeric fiber is chiefly responsible for attachment and internalization of wild-type adenoviruses to their host cells. Within a mature adenoviral capsid, fibers are grounded by close attachment of one end to the penton, but the other end ("knob") of the fiber does not contact any other capsid protein. Thus, the entire fiber forms a spike-like protrusion from the capsid, and amino acid residues within the terminal "knob" domain function as a ligand for cell surface proteins during the process of adenoviral infection. To a lesser extent, the penton also mediates viral attachment through interactions between RGD motifs of the penton and $\alpha_v$-integrins present on virtually all cells.

Given its central role in wild-type adenoviral infection, the majority of the efforts aimed at targeting adenoviruses have focused on modification of the fiber protein (see, e.g., International Patent Applications WO 95/26412 (Curiel et al.), WO 94/10323 (Spooner et al.), WO 94/24299 (Cotten et al.), and U.S. Pat. No. 5,543,328 (McClelland et al.)). These efforts have proven disappointing, largely because they fail to preserve important fiber protein functions, such as stable trimerization and penton base binding (Spooner et al., supra). Moreover, replacement of the fiber knob with a cell-surface ligand (McClelland et al., supra) produces a virus only suitable for infecting a cell type having that ligand. Such a strategy produces a virus having many of the same targeting problems associated with wild-type adenoviruses (in which cellular tropism is mediated by a single protein), thus decreasing the flexibility of the vector. Moreover, due to the integral connection between the fiber trimerization and targeting functions, obtaining a functioning mutant fiber protein with substituted targeting is difficult. For example, removing the fiber knob and replacing it with a non-trimerizing ligand (e.g., Spooner et al., McClelland et al., supra) results in a virus lacking appreciable fiber protein. Considering these drawbacks, there exists a need for improved strategies for targeting adenoviral vectors.

BRIEF SUMMARY OF THE INVENTION

The present invention provides a chimeric protein IX (pIX). The chimeric pIX protein has an adenoviral pIX domain and also a non-native amino acid. Where the non-native amino acid is a ligand that binds to a substrate present on the surface of cells, the chimeric pIX can be used to target vectors containing such proteins to desired cell types. Thus, the invention provides vector systems including such chimeric pIX proteins, as well as methods of infecting cells using such vector systems. These and other aspects of the present invention, as well as additional inventive features, will be apparent upon reading the following detailed description and reviewing the accompanying drawing and sequences.

BRIEF DESCRIPTION OF THE DRAWINGS

FIGS. 1A and 1B set forth a comparison of the amino acid sequences of the pIX proteins from seven adenoviral serotypes (SEQ ID NOs: 1–7) using the J. Hein method with PAM250 residue weight table. Consensus and majority sequences are indicated as SEQ ID NOs: 8 and 9, respectively.

DETAILED DESCRIPTION OF THE INVENTION

Figure 1A:
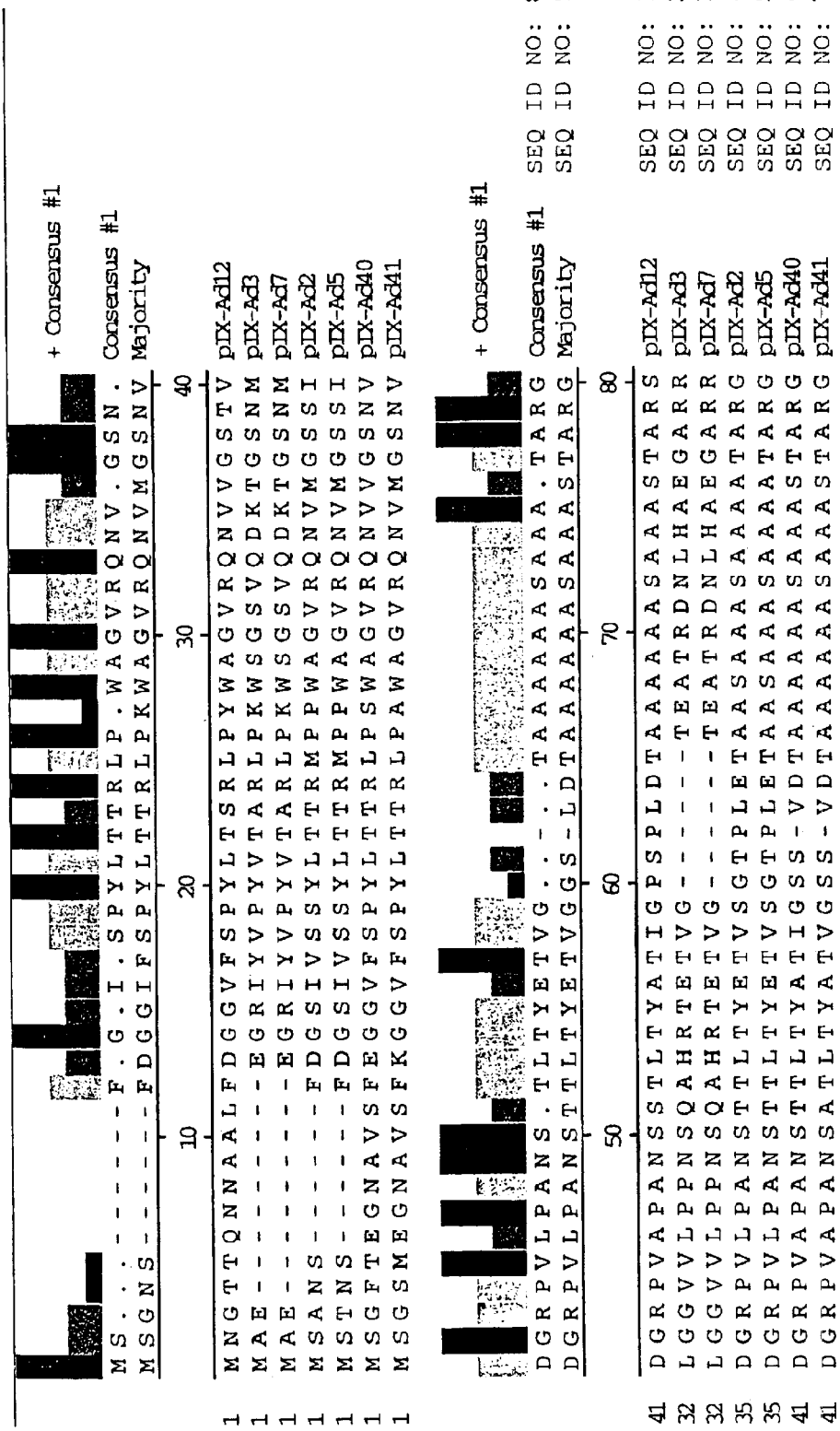

The present invention provides a chimeric adenoviral pIX. The pIX is chimeric in that it has at least one domain derived from an adenoviral pIX, and it also has a domain containing a non-native amino acid sequence. The pIX domain consists essentially of a sequence of a wild-type adenoviral pIX protein, some examples of which are set forth at SEQ ID NOs:1–7; however, the invention is not limited to these exemplary sequences. Indeed, genetic sequences can vary between different strains, and this natural scope of allelic variation is included within the scope of the invention. Thus, a pIX domain typically is at least about 75% homologous to at least about 15 contiguous amino acids of one of SEQ ID NOs:1–7 and preferably is at least about 80% homologous to at least about 15 contiguous amino acids of one of SEQ ID NOs:1–7 (e.g., at least about 85% homologous to at least about 15 contiguous amino acids of one of SEQ ID NOs:1–7); more preferably the domain is at least about 90% homologous to at least about 15 contiguous amino acids of one of SEQ ID NOs:1–7 (such as at least about 95% homologous to at least about 15 contiguous amino acids of one of SEQ ID NOs:1–7), and most preferably the pIX domain is at least about 97% homologous to at least about 15 contiguous amino acids of one of SEQ ID NOs:1–7. Preferably, the homology extends to at least 25 contiguous amino acids, such as at least about 50 contiguous amino acids. Determining the degree of homology, including the possibility for gaps, can be accomplished using any method known to those of skill in the art (e.g., Clustal or J. Hein method using PAM100 or PAM 250 residue weight table, BLASTp, etc.).

Additionally and alternatively, the pIX domain can include one or more mutations (e.g., point mutations, deletions, insertions, etc.) from the exemplary sequences or another naturally occurring pIX protein. Thus, a pIX domain can consist essentially of a truncated adenoviral pIX peptide sequence, for example, truncated by one or more amino acids at the C- or N-terminus. In cases where a mutation is an insertion, the protein can be said to have two pIX domains (i.e., first and second domains) flanking the insertion. Preferably, these domains do not share any common peptide sequences. The inserted sequence can be or comprise a spacer peptide domain or, in some embodiments, a ligand as set forth below. In other embodiments, the protein has only one pIX domain consisting essentially of a full-length adenoviral pIX peptide sequence. Where the pIX sequence contains one or more point mutations, preferably, such a mutation is conservative in that it minimally disrupts the biochemical properties of the pIX domain, particularly the ability of the protein to interact with and become incorporated into adenoviral capsids. Thus, where mutations are introduced to substitute amino acid residues, positively-charged residues (H, K, and R) preferably are substituted with positively-charged residues; negatively-charged residues (D and E) preferably are substituted with negatively-charged residues; neutral polar residues (C, G, N, Q, S, T, and Y) preferably are substituted with neutral polar residues; and neutral non-polar residues (A, F, I, L, M, P, V, and W) preferably are substituted with neutral non-polar residues.

As mentioned, in addition to having at least one pIX domain, the inventive protein also has a non-native amino acid sequence. The non-native amino acid sequence can, but need not, be a discrete domain or stretch of contiguous amino acids. In other words, the non-native amino acid sequence can be generated by the particular confirmation of the protein, e.g., through folding of the protein in such a way as to bring contiguous and/or noncontiguous sequences into mutual proximity. Thus, for example, the non-native amino acid can be constrained by a peptide loop within the chimeric protein (formed, for example, by a disulfide bond between non-adjacent amino acids of said protein). Typically, the protein is a fusion protein in which the non-native amino acid sequence is a discrete domain of the protein fused to the pIX domain. In this configuration, a non-native amino acid sequence can constitute the C- or N-terminus of the protein, or it can be located internally (i.e., between two pIX domains as described above).

The non-native amino acid sequence can be any desired amino acid sequence, so long as it is not native to a wild-type adenoviral pIX protein. While, as mentioned, the sequence can comprise a spacer polypeptide, typically the non-native amino acid is selected to confer a desired function to the protein. For example, in many embodiments, the non-native amino acid sequence is a ligand (i.e., a domain that binds a discrete substrate or class of substrates). However, the non-native amino acid sequence can be other classes of polypeptides (e.g., an antibody or a derivative thereof, such as a single chain antibody (ScAb) or Fab (i.e., a univalent antibody or a fragment of an immunoglobulin consisting of one light chain linked through a disulphide bond to a portion of the heavy chain, containing one antigen binding site), an antigen, an epitope, a glycosylation or phosphorylation signal, a protease recognition sequence, etc.), if desired.

Where the non-native amino acid is a ligand, its inclusion into the chimeric pIX confers the ability for the pIX to recognize and bind to the substrate of the ligand. Thus, the protein can be engineered to recognize any desired substrate. Preferably, the ligand is incorporated within the protein such that it is displayed on the surface of a capsid containing the protein, thus permitting such a capsid to be targeted to a desired substrate via the chimeric pIX protein.

In one embodiment, the ligand binds to a substrate present on the surface of a cell. A cell surface-binding site can be any suitable type of molecule, but typically is a protein (including a modified protein such as a glycoprotein, a mucoprotein, etc.), a carbohydrate, a proteoglycan, a lipid, a mucin molecule, or other similar molecule. Examples of potential cell surface binding sites include, but are not limited to, heparin and chondroitin sulfate moieties found on glycosaminoglycans; sialic acid moieties found on mucins, glycoproteins, and gangliosides; common carbohydrate molecules found in membrane glycoproteins, including mannose, N-acetyl-galactosamine, N-acetyl-glucosamine, fructose, and galactose; glycoproteins such as cell adhesion molecules (CAMs) (e.g., ICAM-1, ICAM-2, ICAM-3, VCAM-1, NCAM), selectins (e.g., E-selectin, P-selectin, L-selectin, etc.), cadherins, TNF family receptors, GPI-linked receptors, receptors that are efficiently internalized (e.g., CD44, CD31 on endothelial cells, CD34 on high endo-venules), endoglin, growth factor receptors, PSA, androgen receptors, glucocorticoid receptors, prostate-specific membrane antigen (PSMA), members of the MUC family (e.g., MUC1, MUC234, MUC5AC, MUC5B, MUC7), KSA, members of the carcino-embryonic antigen (CEA) family (e.g. CEA, non-specific cross-reacting antigen 50/90 (NCA), Biliary Glyco Protein (BGP), and gene family member 2 (CGM2)), HER2/NEU (erbB2), folate receptors, chorionic gonadotropin-$\beta$ (Zhang et al., *Clin. Cancer Res.*, 4, 2669–76 (1998); *Cancer Res.*, 58, 4055 (1998)), and others are known in the art.

A particular cell surface-binding site can be present on a narrow class of cell types (e.g., cardiac muscle, skeletal muscle, smooth muscle, etc.) or a broader group encompassing several cell types. Through integration of an appropriate cell-specific ligand, the virion can be employed to target any desired cell type, such as, for example, neuronal, glial, endothelial (e.g., via tissue factor receptor, FLT-1, CD31, CD36, CD34, CD105, CD13, ICAM-1 (McCormick et al., *J. Biol. Chem.*, 273, 26323–29 (1998)), thrombomodulin receptor (Lupus et al., *Suppl.*, 2, S120 (1998)); VEGFR-3 (Lymboussaki et al., *Am. J Pathol.*, 153(2), 395–403 (1998), mannose receptor; VCAM-1 (Schwarzacher et al., *Atherocsclerosis*, 122, 59–67 (1996)), or other receptors), immune system (e.g., T-cells, B-cells, monocytes, dendritic cells, etc.), blood clot (e.g., through fibrinogen or $\alpha$IIb$\beta$3 peptide), epithelial (e.g., inflamed tissue through selecting, VCAM-1, ICAM-1, etc.), keratinocyte, follicular cell, adipocyte, fibroblast, hematopoietic or other stem cell, myoblast, myofiber, cardiomyocyte, smooth muscle, somatic muscle, osteoclast, osteoblast, tooth blast, chondrocyte, melanocyte, etc., as well as cancer cells derived from any of the above cell types (e.g., prostate (such as via prostate-specific membrane antigen (PSMA) receptor (see, e.g., Schuur et al., *J Biol. Chem.*, 271, 7043 (1996); Liu et al., *Cancer Res.*, 58, 4055 (1998))), breast, lung, brain (e.g., glioblastoma), leukemia/lymphoma, liver, sarcoma, bone, colon, testicular, ovarian, bladder, throat, stomach, pancreas, rectum, skin (e.g., melanoma), kidney, etc.). Thus, the inventive virions can be targeted to cells within any organ or system, including, for example, respiratory system (e.g., trachea, upper airways, lower airways, alveoli), nervous system and sensory organs (e.g., skin, ear, nasal, tongue, eye), digestive system (e.g., oral epithelium and sensory organs, salivary glands, stomach, small intestines/duodenum, colon, gall bladder, pancreas, rectum), muscular system (e.g., skeletal muscle, connective tissue, tendons), skeletal system (e.g., joints (synovial cells), osteoclasts, osteoblasts, etc.), immune system (e.g., bone marrow, stem cells, spleen, thymus, lymphatic system, etc.), circulatory system (e.g., muscles, connective tissue, and/or endothelia of the arteries, veins, capillaries, etc.), reproductive system (e.g., testes, prostate, uterus, ovaries), urinary system (e.g., bladder, kidney, urethra), endocrine or exocrine glands (e.g., breasts, adrenal glands, pituitary glands), etc.

In other embodiments a non-native ligand can be used to purify the virus, to inactivate the virus (e.g., by adsorbing it to a substrate for the ligand), or to grow the virus on cell lines having receptors recognizing the non-native ligand, for example, as described in International Patent Application WO 98/54346 (Wickham et al.). To effect such applications, the non-native ligand can bind a compound other than a cell-surface protein. Thus, the ligand can bind blood- and/or lymph-borne proteins (e.g., albumin), synthetic peptide sequences such as polyamino acids (e.g., polylysine, polyhistidine, etc.), artificial peptide sequences (e.g., FLAG), and RGD peptide fragments (Pasqualini et al., *J Cell. Biol.*, 130, 1189 (1995)). The ligand can even bind non-peptide substrates, such as plastic (e.g., Adey et al., *Gene*, 156, 27 (1995)), biotin (Saggio et al., *Biochem. J.*, 293, 613 (1993)), DNA sequences (Cheng et al., *Gene*, 171, 1 (1996); Krook et al., *Biochem. Biophys., Res. Commun.*, 204, 849 (1994)), streptavidin (Geibel et al., *Biochemistry*, 34, 15430 (1995); Katz, *Biochemistry*, 34, 15421 (1995)), nitrostreptavidin (Balass et al., *Anal. Biochem.*, 243, 264 (1996)), heparin (Wickham et al., *Nature Biotechnol.*, 14, 1570–73 (1996)), cationic supports, metals such as nickel and zinc (e.g., Rebar et al., *Science*, 263, 671 (1994); Qui et al., *Biochemistry*, 33, 8319 (1994)), or other potential substrates.

Examples of suitable ligands and their substrates include, but are not limited to, CR2 receptor and its ligands, CD4 receptor and its ligands among which is the V3 loop of HIV gp120, transferrin receptor and its ligand (transferrin), low density lipoprotein receptor and its ligand, the ICAM-1 receptor on epithelial and endothelial cells in the lungs and its ligand, the CD40 protein found on dendritic cells and an immunoglobulin fragment that binds it or CD40 ligand, linear or cyclic peptide ligands for streptavidin or nitrostreptavidin (Katz, *Biochemistry*, 34, 15421 (1995)), galactin sequences that bind lactose, galactose and other galactose-containing compounds, and asialoglycoproteins that recognize deglycosylated protein ligands. Moreover, additional ligands and their binding sites preferably include (but are not limited to) short (e.g., 6 amino acids or less) linear stretches of amino acids recognized by integrins, as well as polyamino acid sequences such as polylysine, polyarginine, etc. Inserting multiple lysines and/or arginines provides for recognition of heparin and DNA, and an RGD sequence can be used as a ligand to bind integrins. Also, a ligand can comprise a commonly employed peptide tag (e.g., short amino acid sequences known to be recognized by available antisera) such as sequences from glutathione-S-transferase (GST) from *Shistosoma manosi*, thioredoxin β-galactosidase, or maltose binding protein (MPB) from *E. coli*., human alkaline phosphatase, the FLAG octapeptide, hemagglutinin (HA) (Wickham et al. (1996), supra), polyoma virus peptides, the SV40 large T antigen peptide, BPV peptides, the hepatitis C virus core and envelope E2 peptides and single chain antibodies recognizing them (Chan, *J Gen. Virol.*, 77, 2531 (1996)), the c-myc peptide, adenoviral penton base epitopes (Stuart et al., *EMBO J.*, 16, 1189–98 (1997)), epitopes present in the E2 envelope of the hepatitis C virus (see, e.g., Chan et al. (1996), supra), and other commonly employed tags. A preferred substrate for a tag ligand is an antibody directed against it or a derivative of such an antibody (e.g., a Fab fragment or ScAb). For a discussion on the use of peptide tags and their corresponding substrates as a ligand in the context of the present invention, see generally, International Patent Application WO 00/15823 (Wickham et al.).

As mentioned, a suitable ligand can be specific for any desired substrate, such as those recited herein or otherwise known in the art. However, the chimeric pIX can be engineered to include novel ligands by first assaying for the ability of a peptide to interact with a given substrate. Generally, a random or semi-random peptide library containing potential ligands can be produced, which is essentially a library within an expression vector system and can be screened by exposing the expressed proteins (i.e., the putative ligands) to a desired substrate. Positive selective binding of a species within the library to the substrate indicates a ligand for that substrate, at least under the conditions of the assay. For screening such a peptide library, any assay able to detect interactions between proteins and substrates is appropriate, and many are known in the art. However, one preferred assay for screening a protein library is a display system (e.g., using an adenovirus or a bacteriophage), which employs a virus expressing the library (e.g., Koivunen et al., *Bio/Technology*, 13, 265–70 (1995); Yanofsky et al., *Proc. Nat. Acad. Sci. U.S.A.*, 93, 7381–86 (1996); Barry et al., *Nature Med.*, 2(3), 299–305 (1996); and U.S. Pat. No. 5,622,699 (Ruoslahti et al.). Binding of the virus to the substrate is assayed by exposing the virus to the substrate, rinsing the substrate, and selecting for virus remaining bound to the substrate. Subsequently, limiting dilution can identify individual clones expressing the putative ligand. Thereafter, the insert present in such clones can be sequenced to determine the identity of the ligand, if desired.

The chimeric pIX protein of the present invention can be made by any suitable method. For example, the protein can be synthesized using standard direct peptide synthesizing techniques (e.g., as summarized in Bodanszky, Principles of Peptide Synthesis (Springer-Verlag, Heidelberg: 1984)), such as via solid-phase synthesis (see, e.g., Merrifield, *J Am. Chem. Soc.*, 85, 2149–54 (1963); and Barany et al., *Int. J Peptide Protein Res.*, 30, 705–739 (1987)). Alternatively, site-specific mutations can be introduced by ligating into an expression vector a synthesized oligonucleotide comprising the modified site. Alternatively, a plasmid, oligonucleotide, or other vector encoding the desired mutation can be recombined with the adenoviral genome or with an expression vector encoding the pIX protein to introduce the desired mutation. Oligonucleotide-directed site-specific mutagenesis procedures also are appropriate (e.g., Walder et al., *Gene*, 42, 133 (1986); Bauer et al., *Gene*, 37, 73 (1985); Craik, *Biotechniques*, 12–19 (1995); U.S. Pat. Nos. 4,518, 584 (Mark et al.) and 4,737,462 (Mark et al.)).

While any of these methods are appropriate, typically, the protein will be produced by recombinant DNA technology. Thus, the invention provides a nucleic acid encoding the inventive chimeric pIX protein. However engineered, the nucleic acid can be subcloned into an appropriate vector using well-known molecular genetic techniques. When the nucleic acid is operably linked to an appropriate promoter sequence, the nucleic acid can then be transcribed and the peptide subsequently translated in vitro or within a host cell. Any appropriate expression vector (e.g., Pouwels et al., Cloning Vectors: A Laboratory Manual (Elsevior, N.Y.: 1985)) and corresponding suitable host cells can be employed for production of the inventive chimeric pIX protein. Expression hosts include, but are not limited to, bacterial species, yeast, mammalian or insect host cell systems including baculovirus systems (e.g., Luckow et al., *Bio/Technology*, 6, 47 (1988)), and established cell lines such HEK-293, COS-7, C127, 3T3, CHO, HeLa, BHK, etc. An especially preferred expression system is a baculovirus expression system (Wickham et al., *J. Virol.*, 70, 6831–38 (1995)), as it allows the production of high levels of recombinant proteins. Of course, the choice of expression host has ramifications for the type of peptide produced, primarily due to post-translational modification (see generally, O'Reilly et al., Baculovirus Expression Vectors:A Laboratory Manual, W. H. Freeman & Co, Salt Lake City, Utah (1992).

However produced, the chimeric pIX protein can be incorporated into an adenoviral capsid. Thus, the invention provides an adenoviral capsid containing a chimeric pIX protein as described above. In addition to the chimeric pIX protein, the capsid can be further modified, for example, through the inclusion of other recombinant proteins. For example, the capsid can have one or more mutant adenoviral fiber proteins exhibiting reduced affinity for a native adenoviral cellular receptor (typically at least about an order of magnitude less than a wild-type adenoviral fiber protein) (see, e.g., International Patent Application WO 98/54346 (Wickham et al.)). Moreover, the capsid can include one or more recombinant penton base proteins lacking a native RGD sequence to reduce cell binding via a, integrins (see, e.g., U.S. Pat. Nos. 5,559,099 (Wickham et al.) and 5,731,190 (Wickham et al.)). Similarly, the capsid can include one or more recombinant hexons lacking native sequences (e.g., one or more of the hypervariable regions (HVRs) to reduce its ability to be recognized by a neutralizing antibody (see, e.g., International Patent Application WO 98/40509 (Crystal et al.)). Also, the capsid can be modified to reduce its ability to interact with the reticular endothelial system, thereby decreasing its ability to be scavenged by the immune system. For example, capsid proteins can be mutated to lack one or more glycosylation or phosphorylation sites, or capsid proteins can be produced in the presence of inhibitors of glycosylation or phosphorylation. Similarly, the virion proteins can be conjugated to polyethylene glycol to reduce collection and/or opsonin affinity or scavenging by Kupffer cells or other cells of the RES. Such modifications reduce the ability of host animals to develop neutralizing antibodies to the capsid, thereby permitting repeat administration (see, e.g., O'Riordan et al., *Hum. Gene Ther.*, 19(8):1349–1358 (1999); Chillon et al., *Gene Ther.*, 5(7): 995–1002 (1998)). Of course, the hydrophilic polymer PEG is only a preferred polymer and any molecule that sterically blocks recognition of the virion proteins by the host immune system, thus masking the adenoviral vector surface by covalent attachment of the molecule, can be used in the context of the present invention.

Naturally, the capsid can comprise a ligand, such as set forth above, conjugated to, or included within, coat proteins other than pIX (e.g., fiber, a penton, a hexon, protein IIIa or protein VI) (see, e.g., U.S. Pat. Nos. 5,559,099, 5,712,136, 5,731,190, 5,846,782, and 5,770,442 (all to Wickham et al.)). Indeed, where the non-native amino acid sequence in the chimeric pIX protein is also a ligand, the respective ligands can recognize the same substrate, thus increasing the affinity of the entire capsid for the target. Where multiple ligands are present, each can bind to a different substrate. For example, a capsid can comprise a first ligand permitting affinity purification, a second ligand that selectively binds a cell-surface site, and/or a third ligand for inactivating the virus.

Typically, as set forth herein, at least one ligand recognizes a substrate present on the surface of cells, thus permitting the capsid to bind such cells. The capsid can be targeted to any desired cell type, such as those set forth above. Where the capsid is complexed to a nucleic acid, the capsid can be used to deliver the nucleic acid to such cells. Thus, the invention provides a composition of matter comprising an inventive adenoviral capsid and a nucleic acid. The nucleic acid can be complexed to the capsid in any suitable manner. In one embodiment, the nucleic acid is outside the capsid, in which case the composition preferably also includes a liposome to facilitate internalization of the nucleic acid into the cell. In another embodiment, the nucleic acid is encased within the capsid, typically a derivative of an adenoviral genome containing the packaging signal.

Preferably, the nucleic acid is a functioning adenoviral genome, in which instance the composition is an adenoviral vector. The genome need not be complete, and, indeed, the genome preferably contains one or more mutations interfering with viral replication (e.g., in the E1a, E1b, E3, or E4 regions). Most preferably, the vector is replication incompetent except in packaging cells.

For use as a genetic vector, the adenoviral genome includes at least one non-native nucleic acid for transcription, which is operably linked to a promoter. Where the inventive adenoviral vector includes a non-native nucleic acid and a non-adenoviral ligand in its capsid, the non-native nucleic acid can be operably linked to any suitable promoter, such as a promoter native to the adenoviral genome or a non-adenoviral promoter. Where the ligand is employed to deliver the vector to a desired cell type, preferably the non-adenoviral promoter is active within the cell type, and, more preferably, the non-adenoviral promoter is a tissue-specific promoter (e.g., specific for the cell type to which the ligand binds), such as those cell types discussed above. For example, expression in targeted endothelial cells can be mediated using the E-selectin promoter (see, e.g., Whelan et al., *TIBS*, 21, 65–69 (1996)); passenger gene expression in targeted prostate cancer cells can be mediated using the PSA promoter (see, e.g., Schuur et al., *J. Cell Biol.*, 271, 7043 (1996), Pang et al., *Cancer Res.*, 57, 495 (1997)) or the E2F promoter. Furthermore, the promoter can be that controlling a gene encoding a tissue-specific receptor, such as those receptors mentioned herein. Still other tissue specific promoter systems are known in the art. Alternatively, the non-native amino acid can be placed under control of a regulable promoter (e.g., metallothionin promoter, tetracycline-responsive promoter, RU486-responsive promoter, etc.).

The inventive vectors (or libraries of such vectors) can be used to infect cells. Accordingly, the invention provides a method of infecting a cell by contacting a cell with a vector as described above. Where the capsid has a non-native ligand, the vector can be targeted to infect the cell in accordance with the inventive method. Typically, the nucleic acid (e.g., the genome) encodes a protein as discussed above. In such instance, the method permits the nucleic acid to be expressed within the cells to produce the protein. Accordingly, the inventive capsid, vector, and method can be used in gene transfer applications, such as are commonly employed in research and, increasingly, clinical applications. Of course, for delivery into a host (such as an animal), a virus of the present invention can be incorporated into a suitable carrier. As such, the present invention provides a composition comprising a capsid (or library) of the present invention and a pharmacologically acceptable carrier (e.g., a pharmaceutically-acceptable carrier). Any suitable preparation is within the scope of the invention. The exact formulation, of course, depends on the nature of the desired application (e.g., cell type, mode of administration, etc.), and many suitable preparations are set forth in U.S. Pat. No. 5,559,099 (Wickham et al.).

The following examples further illustrate the invention but, of course, should not be construed as in any way limiting its scope. The procedures employed in these examples, such as molecular cloning, sequencing, viral construction, etc., are familiar to those of ordinary skill in this art (see e.g., Sambrook et al., *Molecular Cloning: A Laboratory Manual,* 2d edition, Cold Spring Harbor Press (1989)).

EXAMPLE 1

This example describes two chimeric pIX proteins, each having a non-native ligand.

The Ad5 protein IX gene (SEQ ID NO:5) was mutated to insert an XbaI site at the N and the C termini, respectively. The modified genes were cut with XbaI and ligated to sequences encoding an HA tag. These constructs were sequenced to verify their accuracy. The coding DNA and amino acid sequences of the N-terminal fusion proteins are set forth in SEQ ID NOs:10 and 11, respectively, and coding DNA and amino acid sequences of the and C-terminal fusion proteins are set forth in SEQ ID NOs:12 and 13, respectively. These two proteins are able to bind and recognize HA by virtue of the tag present within the chimeric proteins.

EXAMPLE 2

This example describes targeting cells with chimeric pIX proteins.

The base adenovirus vector, the so-called doubly ablated vector, has a fiber gene with the mutations S to E at position 408 and RLNAEK (SEQ ID NO: 14) to SLNGGG (SEQ ID NO: 15) between the positions 412–417, of the AB loop of the fiber gene, which reduces the affinity of the vector for native cell-surface binding sites (see Roelvink et al., *Science*, 286, 1568–71 (1999)). The penton lacks the sequence RGD present in the RGD loop of wild-type penton proteins, which serves as an internalization sequence for the adenoviral vector. Furthermore, the E1 region in this vector has been replaced with a construct, which consists of a bleomycin resistance gene, and an insect N-defensin gene under control of the *E. coli* lac promoter. The nucleic acids encoding the chimeric protein IX mutants, present on a small and easily manipulated cloning vector, are recombined into the E1 region of the doubly ablated adenoviral vector using methods known to those skilled in the art. This also introduces a CMV promoter-driven marker enzyme gene such as luciferase into the E1 region.

These vectors can be transfected into anti-HA 293 cells that express the anti HA pseudo-receptor (see, e.g., WO 98/54346 (Wickham et al.); Einfeld et al., *J Virol.*, 73, 9130–36 (1999)). To release the virus, after 5 days the cells are freeze-thawed three times, and the virus-containing lysate is passaged onto fresh anti-HA 293 cells. The resultant viruses are further amplified in the anti-HA 293 cells and then purified using standard methods.

To assess the ability of the chimeric pIX protein to effect cell targeting, viruses containing the N- and C-terminal chimeric pIX proteins can be exposed to the anti-HA 293 cells. Wild-type viruses are used as a positive control, and the backbone vector with the mutant fiber and penton proteins is used as a negative control. By virtue of the mutant fiber and penton proteins, the backbone vector exhibits a 1000-fold reduced affinity, as measured by luciferase enzyme assays, for the cells than the wild-type Ad vector. The two vectors containing the chimeric pIX proteins, however, infect the anti-HA 293 cell line with high affinity. When similar experiments are conducted on ordinary 293 cells (lacking the anti-HA pseudo-receptor), the two vectors containing the chimeric pIX proteins exhibit reduced infectivity, similar to the backbone vector. These results indicate that chimeric pIX proteins containing non-native amino acids can effectively target adenoviruses to desired cell types.

All of the references cited herein, including patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly, this invention includes all modifications encompassed within the spirit and scope of the invention as defined by the claims.

What is claimed is:

1. A chimeric pIX protein having at least one adenoviral pIX domain and a non-native amino acid sequence encoding a ligand that binds to a substrate present on the surface of a cell, wherein the non-native amino acid constitutes the C-terminus of the chimeric protein.

2. The chimeric pIX protein of claim 1, wherein the ligand recognizes a CD40 protein.

3. The chimeric pIX protein of claim 1, wherein the ligand is an RGD-containing or polylysine-containing sequence.

4. The chimeric pIX protein of claim 1, wherein the non-native amino acid is constrained by a peptide loop within the chimeric protein.

5. The chimeric pIX protein of claim 1, wherein at least one adenoviral pIX domain consists essentially of an adenoviral pIX peptide sequence truncated at the C-terminus.

6. The chimeric pIX protein of claim 1, wherein at least one adenoviral pIX domain consists essentially of an adenoviral pIX peptide sequence truncated at the N-terminus.

7. The chimeric pIX protein of claim 1, comprising a first adenoviral pIX domain consisting essentially of an adenoviral pIX peptide sequence truncated at the C-terminus and a second adenoviral pIX domain consisting essentially of an adenoviral pIX peptide sequence truncated at the N-terminus.

8. The chimeric pIX protein of claim 1, having only one adenoviral pIX domain consisting essentially of a full-length adenoviral pIX peptide sequence.

9. A nucleic acid encoding the chimeric pIX protein of claim 1.

10. The chimeric pIX protein of claim 4, wherein the loop comprises a disulfide bond between non-adjacent amino acids of the protein.

11. A chimeric pIX protein having at least one adenoviral pIX domain and a non-native amino acid sequence encoding a ligand that binds to a substrate present on the surface of a cell, wherein the non-native amino acid sequence constitutes the N-terminus of the chimeric protein.

12. The chimeric pIX protein of claim 11, wherein the ligand is an RGD-containing or polylysine-containing sequence.

13. The chimeric pIX protein of claim 11, wherein at least one adenoviral pIX domain consists essentially of an adenoviral pIX peptide sequence (a) truncated at the C-terminus, (b) truncated at the N-terminus, or (c) truncated at the C-terminus with a second adenoviral pIX domain consisting essentially of an adenoviral pIX peptide sequence truncated at the N-terminus.

14. The chimeric pIX protein of claim 11, having only one adenoviral pIX domain consisting essentially of a full-length adenoviral pIX peptide sequence.

15. A nucleic acid encoding the chimeric pIX protein of claim 11.

16. The chimeric pIX protein of claim 7, wherein a spacer peptide domain separates the first and the second adenoviral pIX domains.

17. An adenoviral capsid containing a chimeric pIX protein having at least one adenoviral pIX domain and a non-native amino acid sequence, wherein the non-native amino acid sequence constitutes the C-terminus of the chimeric protein.

18. The adenoviral capsid of claim 17, which binds dendritic cells.

19. The adenoviral capsid of claim 17, comprising a mutant adenoviral fiber protein having an affinity for a native adenoviral cellular receptor of at least about an order of magnitude less than a wild-type adenoviral fiber protein.

20. The adenoviral capsid of claim 17, comprising an adenoviral penton base protein having a mutation affecting at least one native RGD sequence.

21. The adenoviral capsid of claim 17, comprising an adenoviral hexon protein having a mutation affecting at least one native HVR sequence.

22. The adenoviral capsid of claim 17, lacking a native glycosylation or phosphorylation site.

23. The adenoviral capsid of claim 17, which is conjugated to polyethylene glycol.

24. The adenoviral capsid of claim 17, which elicits less immunogenicity in a host animal than does a wild-type adenovirus.

25. The adenoviral capsid of claim 17, comprising a second non-adenoviral ligand conjugated to a fiber, a penton, a hexon, a protein IIIa or a protein VI.

26. A composition of matter comprising the adenoviral capsid of claim 17 and a nucleic acid.

27. An adenoviral vector comprising the adenoviral capsid of claim 17 and an adenoviral genome.

28. The adenoviral capsid of claim 25, wherein the non-native amino acid is a ligand and wherein the second non-adenoviral ligand recognizes the same substrate as the non-native amino acid.

29. The adenoviral vector of claim 27, which is replication incompetent.

30. The adenoviral vector of claim 27, which does not productively infect HEK-293 cells.

31. The adenoviral vector of claim 27, wherein the adenoviral genome comprises a non-native nucleic acid for transcription.

32. A method of infecting a cell, comprising contacting a cell with an adenoviral vector of claim 27.

33. The adenoviral vector of claim 31, wherein the non-native nucleic acid for transcription is operably linked to a non-adenoviral promoter.

34. The adenoviral vector of claim 33, wherein the non-adenoviral promoter is a tissue-specific promoter.

35. The adenoviral vector of claim 33, wherein the non-adenoviral promoter is a regulable promoter.

36. A chimeric pIX protein having (i) at least one adenoviral pIX domain consisting essentially of an adenoviral pIX peptide sequence (a) truncated at the C-terminus, (b) truncated at the N-terminus, or (c) truncated at the C-terminus with a second adenoviral pIX domain consisting essentially of an adenoviral pIX peptide sequence truncated at the N-terminus, and (ii) a non-native amino acid sequence encoding an antigen, wherein the non-native amino acid sequence constitutes the C-terminus of the chimeric pIX protein or is located internally within the chimeric pIX protein.

37. The chimeric pIX protein of claim 36, wherein a spacer peptide domain separates the first and the second adenoviral pIX domains.

38. A nucleic acid encoding the chimeric pIX protein of claim 36.

39. An adenoviral capsid containing a chimeric pIX protein having at least one adenoviral pIX domain and a non-native amino acid sequence, wherein the non-native amino acid sequence constitutes the N-terminus of the chimeric protein.

40. The adenoviral capsid of claim 39, comprising an adenoviral penton base protein having a mutation affecting at least one native RGD sequence.

41. An adenoviral vector comprising the adenoviral capsid of claim 39 and an adenoviral genome.

42. A chimeric pIX protein having at least one adenoviral pIX domain and a non-native amino acid sequence encoding a ligand that binds to a substrate present on the surface of a cell, wherein the non-native amino acid sequence is located internally within the chimeric protein, and wherein the ligand is an RGD-containing or polylysine-containing sequence.

43. A chimeric pIX protein having at least one adenoviral pIX domain and a non-native amino acid sequence encoding a ligand that binds to a substrate present on the surface of a cell, wherein the non-native amino acid sequence is located internally within the chimeric protein, and wherein at least one adenoviral pIX domain consists essentially of an adenoviral pIX peptide sequence (a) truncated at the C-terminus, (b) truncated at the N-terminus, or (c) truncated at the C-terminus with a second adenoviral pIX domain consisting essentially of an adenoviral pIX peptide sequence truncated at the N-terminus.

44. The chimeric pIX protein of claim 43, wherein at least one adenoviral pIX domain consists essentially of an adenoviral pIX peptide sequence truncated at the C-terminus with a second adenoviral pIX domain consisting essentially of an adenoviral pIX peptide sequence truncated at the N-terminus, and a spacer peptide domain separates the first and the second adenoviral pIX domains.

45. The chimeric pIX protein of claim 44, wherein the spacer peptide domain comprises the ligand domain.

46. An adenoviral capsid comprising (a) a chimeric pIX protein having at least one adenoviral pIX domain, (b) a non-native amino acid sequence, wherein the non-native amino acid sequence is located internally within the chimeric protein, and (c) an adenoviral penton base protein having a mutation affecting at least one native RGD sequence.

* * * * *

SEQUENCE LISTING

```
<160> NUMBER OF SEQ ID NOS: 15

<210> SEQ ID NO 1
<211> LENGTH: 144
<212> TYPE: PRT
<213> ORGANISM: Adenovirus

<400> SEQUENCE: 1

Met Asn Gly Thr Thr Gln Asn Asn Ala Ala Leu Phe Asp Gly Gly Val
 1               5                  10                  15

Phe Ser Pro Tyr Leu Thr Ser Arg Leu Pro Tyr Trp Ala Gly Val Arg
                20                  25                  30

Gln Asn Val Val Gly Ser Thr Val Asp Gly Arg Pro Val Ala Pro Ala
             35                  40                  45

Asn Ser Ser Thr Leu Thr Tyr Ala Thr Ile Gly Pro Ser Pro Leu Asp
         50                  55                  60

Thr Ala Ala Ala Ala Ala Ser Ala Ala Ala Ser Thr Ala Arg Ser
 65                  70                  75                  80

Met Ala Ala Asp Phe Ser Phe Tyr Asn His Leu Ala Ser Asn Ala Val
                 85                  90                  95
```

```
Thr Arg Thr Ala Val Arg Glu Asp Ile Leu Thr Val Met Leu Ala Lys
            100                 105                 110

Leu Glu Thr Leu Thr Ala Gln Leu Glu Glu Leu Ser Gln Lys Val Glu
        115                 120                 125

Glu Leu Ala Asp Ala Thr Thr His Thr Pro Ala Gln Pro Val Thr Gln
130                 135                 140
```

<210> SEQ ID NO 2
<211> LENGTH: 125
<212> TYPE: PRT
<213> ORGANISM: Adenovirus

<400> SEQUENCE: 2

```
Met Ala Glu Glu Gly Arg Ile Tyr Val Pro Tyr Val Thr Ala Arg Leu
1               5                   10                  15

Pro Lys Trp Ser Gly Ser Val Gln Asp Lys Thr Gly Ser Asn Met Leu
            20                  25                  30

Gly Gly Val Val Leu Pro Pro Asn Ser Gln Ala His Arg Thr Glu Thr
        35                  40                  45

Val Gly Thr Glu Ala Thr Arg Asp Asn Leu His Ala Glu Gly Ala Arg
    50                  55                  60

Arg Pro Glu Asp Gln Thr Pro Tyr Met Ile Leu Val Glu Asp Ser Leu
65                  70                  75                  80

Gly Gly Leu Lys Arg Arg Met Asp Leu Leu Glu Glu Ser Asn Gln Gln
                85                  90                  95

Leu Leu Ala Thr Leu Asn Arg Leu Arg Thr Gly Leu Ala Ala Tyr Val
            100                 105                 110

Gln Ala Asn Leu Val Gly Gly Gln Val Asn Pro Phe Val
        115                 120                 125
```

<210> SEQ ID NO 3
<211> LENGTH: 125
<212> TYPE: PRT
<213> ORGANISM: Adenovirus

<400> SEQUENCE: 3

```
Met Ala Glu Glu Gly Arg Ile Tyr Val Pro Tyr Val Thr Ala Arg Leu
1               5                   10                  15

Pro Lys Trp Ser Gly Ser Val Gln Asp Lys Thr Gly Ser Asn Met Leu
            20                  25                  30

Gly Gly Val Val Leu Pro Pro Asn Ser Gln Ala His Arg Thr Glu Thr
        35                  40                  45

Val Gly Thr Glu Ala Thr Arg Asp Asn Leu His Ala Glu Gly Ala Arg
    50                  55                  60

Arg Pro Glu Asp Gln Thr Pro Tyr Met Ile Leu Val Glu Asp Ser Leu
65                  70                  75                  80

Gly Gly Leu Lys Arg Arg Met Asp Leu Leu Glu Glu Ser Asn Gln Gln
                85                  90                  95

Leu Leu Ala Thr Leu Asn Arg Leu Arg Thr Gly Leu Ala Ala Tyr Val
            100                 105                 110

Gln Ala Asn Leu Val Gly Gly Gln Val Asn Pro Phe Val
        115                 120                 125
```

<210> SEQ ID NO 4
<211> LENGTH: 140
<212> TYPE: PRT
<213> ORGANISM: Adenovirus

-continued

```
<400> SEQUENCE: 4

Met Ser Ala Asn Ser Phe Asp Gly Ser Ile Val Ser Ser Tyr Leu Thr
  1               5                  10                  15

Thr Arg Met Pro Pro Trp Ala Gly Val Arg Gln Asn Val Met Gly Ser
             20                  25                  30

Ser Ile Asp Gly Arg Pro Val Leu Pro Ala Asn Ser Thr Thr Leu Thr
         35                  40                  45

Tyr Glu Thr Val Ser Gly Thr Pro Leu Glu Thr Ala Ala Ser Ala Ala
     50                  55                  60

Ala Ser Ala Ala Ala Ala Thr Ala Arg Gly Ile Val Thr Asp Phe Ala
 65                  70                  75                  80

Phe Leu Ser Pro Leu Ala Ser Ser Ala Ala Ser Arg Ser Ser Ala Arg
                 85                  90                  95

Asp Asp Lys Leu Thr Ala Leu Leu Ala Gln Leu Asp Ser Leu Thr Arg
             100                 105                 110

Glu Leu Asn Val Val Ser Gln Gln Leu Leu Asp Leu Arg Gln Gln Val
         115                 120                 125

Ser Ala Leu Lys Ala Ser Ser Pro Pro Asn Ala Val
     130                 135                 140

<210> SEQ ID NO 5
<211> LENGTH: 140
<212> TYPE: PRT
<213> ORGANISM: Adenovirus

<400> SEQUENCE: 5

Met Ser Thr Asn Ser Phe Asp Gly Ser Ile Val Ser Ser Tyr Leu Thr
  1               5                  10                  15

Thr Arg Met Pro Pro Trp Ala Gly Val Arg Gln Asn Val Met Gly Ser
             20                  25                  30

Ser Ile Asp Gly Arg Pro Val Leu Pro Ala Asn Ser Thr Thr Leu Thr
         35                  40                  45

Tyr Glu Thr Val Ser Gly Thr Pro Leu Glu Thr Ala Ala Ser Ala Ala
     50                  55                  60

Ala Ser Ala Ala Ala Ala Thr Ala Arg Gly Ile Val Thr Asp Phe Ala
 65                  70                  75                  80

Phe Leu Ser Pro Leu Ala Ser Ser Ala Ala Ser Arg Ser Ser Ala Arg
                 85                  90                  95

Asp Asp Lys Leu Thr Ala Leu Leu Ala Gln Leu Asp Ser Leu Thr Arg
             100                 105                 110

Glu Leu Asn Val Val Ser Gln Gln Leu Leu Asp Leu Arg Gln Gln Val
         115                 120                 125

Ser Ala Leu Lys Ala Ser Ser Pro Pro Asn Ala Val
     130                 135                 140

<210> SEQ ID NO 6
<211> LENGTH: 132
<212> TYPE: PRT
<213> ORGANISM: Adenovirus

<400> SEQUENCE: 6

Met Ser Gly Phe Thr Glu Gly Asn Ala Val Ser Phe Glu Gly Gly Val
  1               5                  10                  15

Phe Ser Pro Tyr Leu Thr Thr Arg Leu Pro Ser Trp Ala Gly Val Arg
             20                  25                  30

Gln Asn Val Val Gly Ser Asn Val Asp Gly Arg Pro Val Ala Pro Ala
```

-continued

```
                    35                  40                  45
Asn Ser Thr Thr Leu Thr Tyr Ala Thr Ile Gly Ser Ser Val Asp Thr
     50                  55                  60
Ala Ala Ala Ala Ala Ser Ala Ala Ser Thr Ala Arg Gly Met
 65                  70                  75                  80
Ala Ala Asp Phe Gly Leu Tyr Asn Gln Leu Ala Ala Ser Arg Leu Arg
                 85                  90                  95
Glu Glu Asp Ala Leu Ser Val Val Leu Thr Arg Leu Glu Glu Leu Ser
            100                 105                 110
Gln Gln Leu Gln Asp Met Ser Ala Lys Met Ala Leu Leu Asn Pro Pro
        115                 120                 125
Ala Asn Thr Ser
    130

<210> SEQ ID NO 7
<211> LENGTH: 133
<212> TYPE: PRT
<213> ORGANISM: Adenovirus

<400> SEQUENCE: 7

Met Ser Gly Ser Met Glu Gly Asn Ala Val Ser Phe Lys Gly Val
  1               5                  10                  15
Phe Ser Pro Tyr Leu Thr Thr Arg Leu Pro Ala Trp Ala Gly Val Arg
                 20                  25                  30
Gln Asn Val Met Gly Ser Asn Val Asp Gly Arg Pro Val Ala Pro Ala
             35                  40                  45
Asn Ser Ala Thr Leu Thr Tyr Ala Thr Val Gly Ser Ser Val Asp Thr
     50                  55                  60
Ala Ala Ala Ala Ala Ser Ala Ala Ser Thr Ala Arg Gly Met
 65                  70                  75                  80
Ala Ala Asp Phe Gly Leu Tyr Asn Gln Leu Ala Ala Ser Arg Ser Leu
                 85                  90                  95
Arg Glu Glu Asp Ala Leu Ser Val Val Leu Thr Arg Met Glu Glu Leu
            100                 105                 110
Ser Gln Gln Leu Gln Asp Leu Phe Ala Lys Val Ala Leu Leu Asn Pro
        115                 120                 125
Pro Ala Asn Ala Ser
    130

<210> SEQ ID NO 8
<211> LENGTH: 130
<212> TYPE: PRT
<213> ORGANISM: Adenovirus
<220> FEATURE:
<221> NAME/KEY: misc_feature
<222> LOCATION: (2)..(5)
<223> OTHER INFORMATION: "Xaa" may be any amino acid
<220> FEATURE:
<221> NAME/KEY: misc_feature
<222> LOCATION: (7)..(7)
<223> OTHER INFORMATION: "Xaa" may be any amino acid
<220> FEATURE:
<221> NAME/KEY: misc_feature
<222> LOCATION: (9)..(9)
<223> OTHER INFORMATION: "Xaa" may be any amino acid
<220> FEATURE:
<221> NAME/KEY: misc_feature
<222> LOCATION: (11)..(11)
<223> OTHER INFORMATION: "Xaa" may be any amino acid
<220> FEATURE:
<221> NAME/KEY: misc_feature
<222> LOCATION: (21)..(21)
```

-continued

```
<223> OTHER INFORMATION: "Xaa" may be any amino acid
<220> FEATURE:
<221> NAME/KEY: misc_feature
<222> LOCATION: (30)..(30)
<223> OTHER INFORMATION: "Xaa" may be any amino acid
<220> FEATURE:
<221> NAME/KEY: misc_feature
<222> LOCATION: (34)..(34)
<223> OTHER INFORMATION: "Xaa" may be any amino acid
<220> FEATURE:
<221> NAME/KEY: misc_feature
<222> LOCATION: (45)..(45)
<223> OTHER INFORMATION: "Xaa" may be any amino acid
<220> FEATURE:
<221> NAME/KEY: misc_feature
<222> LOCATION: (54)..(57)
<223> OTHER INFORMATION: "Xaa" may be any amino acid
<220> FEATURE:
<221> NAME/KEY: misc_feature
<222> LOCATION: (69)..(69)
<223> OTHER INFORMATION: "Xaa" may be any amino acid
<220> FEATURE:
<221> NAME/KEY: misc_feature
<222> LOCATION: (74)..(76)
<223> OTHER INFORMATION: "Xaa" may be any amino acid
<220> FEATURE:
<221> NAME/KEY: misc_feature
<222> LOCATION: (79)..(83)
<223> OTHER INFORMATION: "Xaa" may be any amino acid
<220> FEATURE:
<221> NAME/KEY: misc_feature
<222> LOCATION: (86)..(86)
<223> OTHER INFORMATION: "Xaa" may be any amino acid
<220> FEATURE:
<221> NAME/KEY: misc_feature
<222> LOCATION: (88)..(90)
<223> OTHER INFORMATION: "Xaa" may be any amino acid
<220> FEATURE:
<221> NAME/KEY: misc_feature
<222> LOCATION: (92)..(95)
<223> OTHER INFORMATION: "Xaa" may be any amino acid
<220> FEATURE:
<221> NAME/KEY: misc_feature
<222> LOCATION: (98)..(98)
<223> OTHER INFORMATION: "Xaa" may be any amino acid
<220> FEATURE:
<221> NAME/KEY: misc_feature
<222> LOCATION: (100)..(101)
<223> OTHER INFORMATION: "Xaa" may be any amino acid
<220> FEATURE:
<221> NAME/KEY: misc_feature
<222> LOCATION: (105)..(105)
<223> OTHER INFORMATION: "Xaa" may be any amino acid
<220> FEATURE:
<221> NAME/KEY: misc_feature
<222> LOCATION: (107)..(108)
<223> OTHER INFORMATION: "Xaa" may be any amino acid
<220> FEATURE:
<221> NAME/KEY: misc_feature
<222> LOCATION: (110)..(112)
<223> OTHER INFORMATION: "Xaa" may be any amino acid
<220> FEATURE:
<221> NAME/KEY: misc_feature
<222> LOCATION: (114)..(116)
<223> OTHER INFORMATION: "Xaa" may be any amino acid
<220> FEATURE:
<221> NAME/KEY: misc_feature
<222> LOCATION: (119)..(120)
<223> OTHER INFORMATION: "Xaa" may be any amino acid
<220> FEATURE:
<221> NAME/KEY: misc_feature
<222> LOCATION: (122)..(125)
<223> OTHER INFORMATION: "Xaa" may be any amino acid
<220> FEATURE:
<221> NAME/KEY: misc_feature
<222> LOCATION: (127)..(127)
<223> OTHER INFORMATION: "Xaa" may be any amino acid
<220> FEATURE:
<221> NAME/KEY: misc_feature
```

<222> LOCATION: (129)..(129)
<223> OTHER INFORMATION: "Xaa" may be any amino acid

<400> SEQUENCE: 8

```
Met Ser Xaa Xaa Xaa Phe Xaa Gly Xaa Ile Xaa Ser Pro Tyr Leu Thr
  1               5                  10                  15

Thr Arg Leu Pro Xaa Trp Ala Gly Val Arg Gln Asn Val Xaa Gly Ser
             20                  25                  30

Asn Xaa Asp Gly Arg Pro Val Leu Pro Ala Asn Ser Xaa Thr Leu Thr
         35                  40                  45

Tyr Glu Thr Val Gly Xaa Xaa Xaa Xaa Thr Ala Ala Ala Ala Ala Ala
 50                  55                  60

Ser Ala Ala Xaa Thr Ala Arg Gly Xaa Xaa Xaa Asp Phe Xaa Xaa
 65                  70                  75                  80

Xaa Xaa Xaa Leu Ala Xaa Ser Xaa Xaa Xaa Arg Xaa Xaa Xaa Xaa Glu
                 85                  90                  95

Asp Xaa Leu Xaa Xaa Leu Leu Ala Xaa Leu Xaa Xaa Leu Xaa Xaa Xaa
            100                 105                 110

Leu Xaa Xaa Xaa Ser Gln Xaa Xaa Leu Xaa Xaa Xaa Xaa Pro Xaa Asn
        115                 120                 125

Xaa Val
    130
```

<210> SEQ ID NO 9
<211> LENGTH: 130
<212> TYPE: PRT
<213> ORGANISM: Adenovirus

<400> SEQUENCE: 9

```
Met Ser Gly Asn Ser Phe Asp Gly Gly Ile Phe Ser Pro Tyr Leu Thr
  1               5                  10                  15

Thr Arg Leu Pro Lys Trp Ala Gly Val Arg Gln Asn Val Met Gly Ser
             20                  25                  30

Asn Val Asp Gly Arg Pro Val Leu Pro Ala Asn Ser Thr Thr Leu Thr
         35                  40                  45

Tyr Glu Thr Val Gly Gly Ser Leu Asp Thr Ala Ala Ala Ala Ala Ala
 50                  55                  60

Ser Ala Ala Ser Thr Ala Arg Gly Met Ala Ala Asp Phe Gly Phe
 65                  70                  75                  80

Tyr Asn Leu Leu Ala Ser Ser Ala Gly Gly Arg Ser Ser Ala Arg Glu
                 85                  90                  95

Asp Ala Leu Thr Val Leu Leu Ala Thr Leu Glu Ser Leu Thr Thr Gln
            100                 105                 110

Leu Ala Ala Val Ser Gln Ala Ala Leu Val Gly Gly Ser Pro Pro Asn
        115                 120                 125

Ala Val
    130
```

<210> SEQ ID NO 10
<211> LENGTH: 498
<212> TYPE: DNA
<213> ORGANISM: Adenovirus

<400> SEQUENCE: 10

```
atgtctagat accoctacga cgtgcccgac tacgccggtt ctggctcagg ctccggttca    60
ggttcgggat ctactagaag caccaactcg tttgatggaa gcattgtgag ctcatatttg   120
```

-continued

| | |
|---|---|
| acaacgcgca tgcccccatg ggccggggtg cgtcagaatg tgatgggctc cagcattgat | 180 |
| ggtcgccccg tcctgcccgc aaactctact accttgacct acgagaccgt gtctggaacg | 240 |
| ccgttggaga ctgcagcctc cgccgccgct cagccgctg cagccaccgc cgcgggatt | 300 |
| gtgactgact tgctttcct gagcccgctt gcaagcagtg cagcttcccg ttcatccgcc | 360 |
| cgcgatgaca agttgacggc tcttttggca caattggatt ctttgacccg ggaacttaat | 420 |
| gtcgtttctc agcagctgtt ggatctgcgc agcaggttt ctgccctgaa ggcttcctcc | 480 |
| cctcccaatg cggtttaa | 498 |

<210> SEQ ID NO 11
<211> LENGTH: 165
<212> TYPE: PRT
<213> ORGANISM: Adenovirus

<400> SEQUENCE: 11

Met Ser Arg Tyr Pro Tyr Asp Val Pro Asp Tyr Ala Gly Ser Gly Ser
1               5                   10                  15

Gly Ser Gly Ser Gly Ser Gly Ser Thr Arg Ser Thr Asn Ser Phe Asp
            20                  25                  30

Gly Ser Ile Val Ser Ser Tyr Leu Thr Thr Arg Met Pro Pro Trp Ala
        35                  40                  45

Gly Val Arg Gln Asn Val Met Gly Ser Ser Ile Asp Gly Arg Pro Val
    50                  55                  60

Leu Pro Ala Asn Ser Thr Thr Leu Thr Tyr Glu Thr Val Ser Gly Thr
65                  70                  75                  80

Pro Leu Glu Thr Ala Ala Ser Ala Ala Ala Ser Ala Ala Ala Ala Thr
                85                  90                  95

Ala Arg Gly Ile Val Thr Asp Phe Ala Phe Leu Ser Pro Leu Ala Ser
            100                 105                 110

Ser Ala Ala Ser Arg Ser Ser Ala Arg Asp Asp Lys Leu Thr Ala Leu
        115                 120                 125

Leu Ala Gln Leu Asp Ser Leu Thr Arg Glu Leu Asn Val Val Ser Gln
    130                 135                 140

Gln Leu Leu Asp Leu Arg Gln Gln Val Ser Ala Leu Lys Ala Ser Ser
145                 150                 155                 160

Pro Pro Asn Ala Val
                165

<210> SEQ ID NO 12
<211> LENGTH: 495
<212> TYPE: DNA
<213> ORGANISM: Adenovirus

<400> SEQUENCE: 12

| | |
|---|---|
| atgagcacca actcgtttga tggaagcatt gtgagctcat atttgacaac gcgcatgccc | 60 |
| ccatgggccg ggtgcgtca gaatgtgatg gctccagca ttgatggtcg ccccgtcctg | 120 |
| cccgcaaact ctactacctt gacctacgag accgtgtctg gaacgccgtt ggagactgca | 180 |
| gcctccgccg ccgcttcagc cgctgcagcc accgccgcg ggattgtgac tgactttgct | 240 |
| ttcctgagcc cgcttgcaag cagtgcagct tcccgttcat ccgccgcga tgacaagttg | 300 |
| acggctcttt tggcacaatt ggattctttg acccgggaac ttaatgtcgt ttctcagcag | 360 |
| ctgttggatc tgcgccagca ggtttctgcc ctgaaggctt cctcccctcc caatgcggtt | 420 |
| tctagtggtt ctggctcagg ctccggttca ggttcgggat cttacccta cgacgtgccc | 480 |

-continued

```
gactacgcct ctaga                                                495
```

```
<210> SEQ ID NO 13
<211> LENGTH: 165
<212> TYPE: PRT
<213> ORGANISM: Adenovirus

<400> SEQUENCE: 13

Met Ser Thr Asn Ser Phe Asp Gly Ser Ile Val Ser Ser Tyr Leu Thr
 1               5                  10                  15

Thr Arg Met Pro Pro Trp Ala Gly Val Arg Gln Asn Val Met Gly Ser
            20                  25                  30

Ser Ile Asp Gly Arg Pro Val Leu Pro Ala Asn Ser Thr Thr Leu Thr
        35                  40                  45

Tyr Glu Thr Val Ser Gly Thr Pro Leu Glu Thr Ala Ala Ser Ala Ala
    50                  55                  60

Ala Ser Ala Ala Ala Ala Thr Ala Arg Gly Ile Val Thr Asp Phe Ala
65                  70                  75                  80

Phe Leu Ser Pro Leu Ala Ser Ser Ala Ala Ser Arg Ser Ser Ala Arg
                85                  90                  95

Asp Asp Lys Leu Thr Ala Leu Leu Ala Gln Leu Asp Ser Leu Thr Arg
            100                 105                 110

Glu Leu Asn Val Val Ser Gln Gln Leu Leu Asp Leu Arg Gln Gln Val
        115                 120                 125

Ser Ala Leu Lys Ala Ser Ser Pro Pro Asn Ala Val Ser Ser Gly Ser
    130                 135                 140

Gly Ser Gly Ser Gly Ser Gly Ser Gly Ser Tyr Pro Tyr Asp Val Pro
145                 150                 155                 160

Asp Tyr Ala Ser Arg
                165

<210> SEQ ID NO 14
<211> LENGTH: 6
<212> TYPE: PRT
<213> ORGANISM: Adenovirus

<400> SEQUENCE: 14

Arg Leu Asn Ala Glu Lys
 1               5

<210> SEQ ID NO 15
<211> LENGTH: 6
<212> TYPE: PRT
<213> ORGANISM: Adenovirus

<400> SEQUENCE: 15

Ser Leu Asn Gly Gly Gly
 1               5
```